US012797536B2

(12) United States Patent
Yang

(10) Patent No.: US 12,797,536 B2
(45) **Date of Patent: *Nov. 17, 2026**

(54) DRIVING MECHANISM OF DRUG INFUSION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 797 days.

This patent is subject to a terminal disclaimer.

(21) Appl. No.: 18/034,389

(22) PCT Filed: Jun. 8, 2021

(86) PCT No.: PCT/CN2021/098809

§ 371 (c)(1),
(2) Date: Apr. 28, 2023

(87) PCT Pub. No.: WO2022/110758

PCT Pub. Date: Jun. 2, 2022

(65) Prior Publication Data

US 2023/0405219 A1 Dec. 21, 2023

(30) Foreign Application Priority Data

Nov. 27, 2020 (WO) ................ PCT/CN2020/132037
Dec. 4, 2020 (WO) ................ PCT/CN2020/133736

(51) Int. Cl.
*A61M 5/142* (2006.01)

(52) U.S. Cl.
CPC .... *A61M 5/14212* (2013.01); *A61M 5/14248* (2013.01); *A61M 2005/14208* (2013.01); *A61M 2205/82* (2013.01)

(58) Field of Classification Search
CPC ............ A61M 5/1452; A61M 5/14248; A61M 2005/14208; A61M 2205/82
See application file for complete search history.

(56) References Cited

U.S. PATENT DOCUMENTS 7,144,384 B2 * 12/2006 Gorman .............. A61M 5/1452 604/151
2004/0153032 A1 * 8/2004 Garribotto ........ A61M 5/14248 604/131

(Continued)

FOREIGN PATENT DOCUMENTS

CN 103260678 8/2013
CN 106139311 11/2016

(Continued)

OTHER PUBLICATIONS

"International Search Report (Form PCT/ISA/210) of PCT/CN2021/098809," mailed on Sep. 7, 2021, pp. 1-3.

*Primary Examiner* — Jake Cook
(74) *Attorney, Agent, or Firm* — JCIP GLOBAL INC.

(57) ABSTRACT

A drive mechanism includes at least one driving unit, at least one driving wheel, a linear actuator, a switch unit group and a power supply. The driving unit moves in a driving direction and drives the driving wheel to rotate. The linear actuator pulls the driving unit to move in the driving direction after being powered. The switch unit group comprises a first switch unit and a second switch unit. The first switch is electrically connected with the linear actuator. The power supply, the switch unit group and the linear actuator are electrically connected to form a power supply circuit that supplies power to the linear actuator. When the linear actuator is powered, the driving unit driving, and the driving unit triggers a first signal indicating the end point of the driving direction.

11 Claims, 4 Drawing Sheets

(56) References Cited

U.S. PATENT DOCUMENTS

| | | | | |
|---|---|---|---|---|
| 2009/0012359 | A1* | 1/2009 | Tanaka | A61B 1/00158 600/114 |
| 2019/0117881 | A1 | 4/2019 | Yang | |
| 2022/0143304 | A1* | 5/2022 | Yang | A61M 5/14248 |

FOREIGN PATENT DOCUMENTS

| | | |
|---|---|---|
| CN | 111939371 | 11/2020 |
| CN | 111939386 | 11/2020 |
| CN | 111939387 | 11/2020 |
| WO | 2020233128 | 11/2020 |

* cited by examiner

DRIVING MECHANISM OF DRUG INFUSION DEVICE

CROSS-REFERENCE TO RELATED APPLICATION

This application is a 371 of international application of PCT application serial no. PCT/CN2021/098809, filed on Jun. 8, 2021, which claims the priority benefit of PCT application no. PCT/CN2020/132037, filed on Nov. 27, 2020 and PCT application no. PCT/CN2020/133736, filed on Dec. 4, 2020. The entirety of each of the above-mentioned patent applications is hereby incorporated by reference herein and made a part of this specification.

TECHNICAL FIELD

The present invention mainly relates to the field of medical instruments, in particular to a driving mechanism of a drug infusion device.

BACKGROUND

The pancreas in a normal person can automatically monitor the amount of glucose in the blood and automatically secrete the required dosage of insulin/glucagon. However, for diabetic patients, the function of the pancreas is abnormal, and the pancreas cannot normally secrete required dosage of insulin. Therefore, diabetes is a metabolic disease caused by abnormal pancreatic function and also a lifelong disease. At present, medical technology cannot cure diabetes, but can only control the onset and development of diabetes and its complications by stabilizing blood glucose.

Patients with diabetes need to check their blood glucose before injecting insulin into the body. At present, most of the detection methods can continuously detect blood glucose, and send the blood glucose data to the remote device in real time for the user to view. This detection method is called Continuous Glucose Monitoring (CGM), which requires the detection device to be attached to the surface of the patients' skin, and the sensor carried by the device is inserted into the subcutaneous tissue fluid for testing. According to the blood glucose (BG) level, the infusion device, as a closed-loop or semi-closed-loop artificial pancreas, injects the currently required insulin dose.

However, the current driving mechanism of the drug infusion device has a relatively large power consumption, which raises the requirements on the power supply, and has poor reliability.

Therefore, the prior art urgently needs a drug infusion device with low power consumption and high reliability.

BRIEF SUMMARY OF THE INVENTION

The embodiment of the present invention discloses a driving mechanism of a drug infusion device, the first switch unit controls the power to the linear actuator directly, and the timer controls the power supply circuit by the second switch unit, reducing the power consumption of the infusion device.

The invention discloses a driving mechanism of a drug infusion device, which comprises: at least one driving unit and at least one driving wheel, the driving unit, moving in the driving direction, can drive the driving wheel to rotate; a linear actuator, electrically connected with the driving unit, pulling the driving unit to move in the driving direction after being powered; a switch unit group, at least comprising a first switch unit and a second switch unit, the first switch unit electrically connected with the linear actuator; a power supply, the power supply, the switch unit group and the linear actuator are electrically connected to form a power supply circuit that supplies power to the linear actuator; when the linear actuator is powered, the driving unit implements driving, and the driving unit can trigger a first signal, indicating the end point of the driving direction, the first switch unit receiving the first signal to turn off to cut off the power to the linear actuator; and a program unit, including a timer electrically connected to the second switch unit, the timer controlling the second switch unit to turn off to cut off the power supply circuit.

According to one aspect of the present invention, the driving unit includes at least one driving portion, the driving wheel is provided with wheel teeth which can be pushed by the driving portion to drive the driving wheel.

According to one aspect of the present invention, the movement mode of the driving unit includes linear reciprocating movement or rotary reciprocating movement.

According to one aspect of the present invention, the driving unit includes two driving portions while the driving wheel includes two sub-wheels, and the two driving portions respectively cooperate with different sub-wheels, and the driving unit respectively drives different sub-wheels to rotate in two directions of the reciprocating rotation.

According to one aspect of the present invention, it also includes at least one blocking wall, and the driving unit reaches the movement end of the driving direction when contacts the blocking wall, and during the process of the driving unit moving in one entire driving direction, the movement time of the driving unit is t while the working time of the timer is T, then T≥t.

According to one aspect of the present invention, 0 ms≤T−t≤30 ms.

According to one aspect of the present invention, it further includes an elastic member, and the reciprocating movement includes a driving direction and a resetting direction, and the elastic member applies a resetting and resilience force to the driving unit.

According to one aspect of the present invention, it further includes an electrical connection point located on the power supply circuit between the linear actuator and the first switch unit, and the program unit is electrically connected to the electrical connection point to obtain a second signal, a voltage changing signal, of the electrical connection point.

According to one aspect of the present invention, the switch unit includes a MOS field effect transistor, an analog switch or a relay.

According to one aspect of the present invention, the linear actuator is a shape memory alloy.

According to one aspect of the present invention, the driving unit includes a variety of different reciprocating frequencies, a variety of different reciprocating speeds, or a variety of different movement amplitudes.

Compared with the prior art, the technical solution of the present invention has the following advantages:

In the driving mechanism of the drug infusion device disclosed in the present invention, the power supply, the switch unit group and the linear actuator are electrically connected to form a power supply circuit that supplies power to the linear actuator; when the linear actuator is powered, the driving unit implements driving, and the driving unit can trigger a first signal, indicating the end point of the driving direction, the first switch unit receiving the first signal to turn off to cut off the power to the linear actuator; a program unit, including a timer electrically connected to the second switch unit, the timer controlling the second switch unit to turn off to cut off the power supply circuit, shortening the powered time to the linear actuator and reducing the power consumption of the infusion device. In addition, shortening the powered time to the linear actuator also reduces the probability of fatigue fracture of the linear actuator, improving the safety of the driving and the infusion reliability of the infusion device.

Furthermore, the driving unit includes two driving portions while the driving wheel includes two sub-wheels, and the two driving portions respectively cooperate with different sub-wheels, and the driving unit respectively drives different sub-wheels to rotate in two directions of the reciprocating rotation. The driving unit drives different sub-wheels to rotate in the two reciprocating directions respectively, which improves the infusion efficiency.

Furthermore, the elastic member applies a resetting and resilience force to the driving unit, making the driving unit move in the resetting direction. The elastic member can reset the driving unit automatically without consuming electric energy, which further reduces the power consumption of the infusion device.

Furthermore, it further includes an electrical connection point, and the program unit is connected to the electrical connection point to receive electrical signal. The program can unit continuously adjusts the preset time of the timer through the received electrical signal, making the preset time of the timer infinitely close to the time of the driving unit costed from the start of rotation in the driving direction to it contacts with the blocking wall, which reduces the power consumption of the infusion device and improves the reliability of the infusion device.

DETAILED DESCRIPTION

Figure 1:
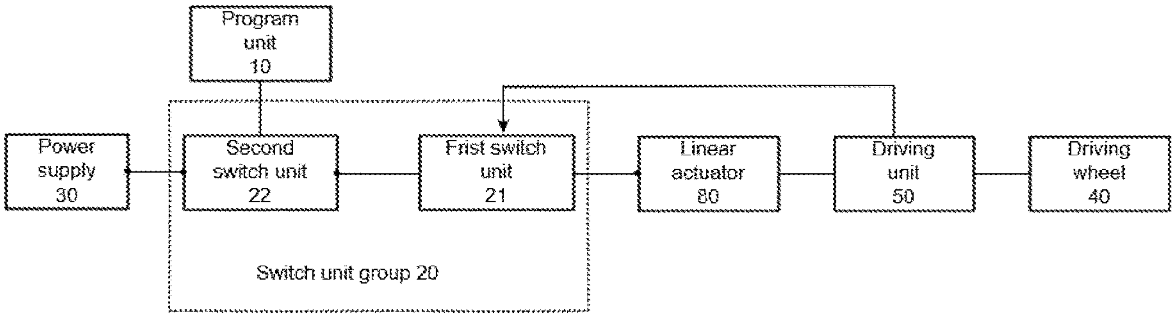
FIG. 1 is a schematic diagram of the connection relationship between the unit modules of the driving mechanism of a drug infusion device according to an embodiment of the present invention.

As mentioned above, the current driving mechanism of the drug infusion device has a relatively large power consumption, which raises the requirements on the power supply, and has poor reliability.

It is found through research that the reason for the above problems is that the linear actuator is fully controlled by the program unit to be powered on or off. Because the program unit needs a longer response time, the linear actuator takes longer to be powered on, thereby consuming more power.

In order to solve this problem, the present invention provides a driving mechanism of a drug infusion device, the first switch unit controls the power to the linear actuator directly, and the timer controls the power supply circuit by the second switch unit, reducing the power consumption of the infusion device.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the figures are not necessarily drawn in the actual scale relationship, for example, the thickness, width, length or distance of certain units may be exaggerated relative to other mechanisms.

The following description of the exemplary embodiment is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in following description of the drawings.

FIG. 1 is a schematic diagram of the connection relationship between the unit modules of the driving mechanism of the drug infusion device according to the embodiment of the present invention.

The drug infusion device includes an infusion needle, a drug storage unit, a piston arranged in the drug storage unit, a screw connected with the piston, a driving mechanism, and the like. The advancement of the screw can directly push the piston forward to achieve drug infusion.

The driving mechanism of the drug infusion device includes a power supply 30, a program unit 10, a switch unit group 20, a linear actuator 80, at least one driving unit 50 and at least one driving wheel 40.

The power supply 30 is used to supply the power to the linear actuator 80. The linear actuator 80 and the driving unit 50 are connected to each other. The power supply 30, the switch unit group 20 and the linear actuator 80 are electrically connected to form a power supply circuit for supplying the power to the linear actuator 80.

The program unit 10 is used to control certain functional units in the infusion device to perform corresponding functions, such as including but not limited to controlling to open and close the second switch unit 22, detecting the amount of the remaining drug, warning, and priming the infusion needle.

The first switch unit 21 is used to control to turn on or disconnect the power to the linear actuator 80. The switch unit group 20 includes MOS field effect transistor, an analog switch or a relay. Preferably, in the embodiment of the present invention, the switch unit is a MOS field effect transistor, which controls the conduction and disconnection of the channel according to the voltage change applied to the gate, thereby realizing the connection and disconnection of the power supply circuit.

What needs to be explained here is that "cutting off the power to the linear actuator" and "disconnecting the power supply circuit to the linear actuator" have completely different meanings. "Cutting off the power to the linear actuator" refers to directly removing the power supplied to the linear actuator, thereby stopping applying the driving force to the driving unit. For example, the turning off of the first switch unit directly stops the linear actuator from being powered. However, "disconnecting the power supply circuit to the linear actuator" only refers to disconnecting the power supply circuit, that is, not necessarily directly remove the power to the linear actuator. For example, the program unit as described below controls the disconnection of the power supply circuit.

The linear actuator 80 is used to apply driving force to the driving unit 50 for movement. When powered on, the physical form of the material of the linear actuator 80 changes, which makes shrinkage deformation of the linear actuator 80 occur, thereby exerting the driving force to move the driving unit 50. The higher the current is, the larger the shrinkage deformation of the linear actuator 80 occurs, and the greater the driving force outputs. Obviously, when the current is constant, the driving force output by the linear actuator 80 is also constant, because of which the linear actuator 80 can output stable and controllable infusion driving force. Obviously, in the embodiment of the present invention, the higher the current is, the faster the driving unit 50 moves; the longer the power-on time is, the greater the amplitude of the driving unit 50's movement is; and the greater the frequency of alternate power-on and power-off is, the greater the frequency of the driving unit 50 reciprocates. Therefore, the infusion device has multiple different infusion modes, such as different infusion rates or different infusion increments, which will be described below.

Preferably, the linear actuator 80 is an electrically driven linear actuator or an electrically heated linear actuator. By alternately being powered on and off, the linear actuator 80 outputs power in pulses. Preferably, in the embodiment of the present invention, the linear actuator 80 is a shape memory alloy.

The driving unit can drive the driving wheel 40 to rotate, thereby realizing drug infusion. In the embodiment of the present invention, the driving unit 50 includes at least one driving portion (like 151 in FIG. 2), and wheel teeth are provided on the driving wheel 40. Therefore, the driving portion can push the wheel teeth to drive the driving wheel 40 to rotate, thereby driving the screw to advance. Preferably, in the embodiment of the present invention, a driving portion is provided on the driving unit 50, and the driving wheel 40 is a ratchet wheel with ratchet teeth. The ratchet teeth can be pushed more easily, improving driving efficiency.

The movement mode of the driving unit 50 includes linear reciprocating movement or rotary reciprocating movement. Preferably, in the embodiment of the present invention, the driving unit 50 rotates reciprocating around a fixed shaft. The driving mechanism is also provided with an elastic member (like 170 in FIG. 2) for applying a resetting and resilience force to the driving unit 50. When the driving unit 50 moves in the driving direction, the elastic member exerts an ever-increasing resetting and resilience force to the driving unit 50. The elastic member can reset the driving unit 50 automatically without consuming electric energy which reduces the power consumption of the infusion device. Preferably, the elastic member is a spring.

Under the cooperation of the elastic member and the linear actuator 80, the driving unit 50 performs a rotary reciprocating movement. And the driving unit 50 can push the wheel teeth when it moves in the driving direction, and it stops pushing the wheel teeth while moving in the resetting direction, which will be described in detail below in conjunction with FIG. 2.

Figure 6:
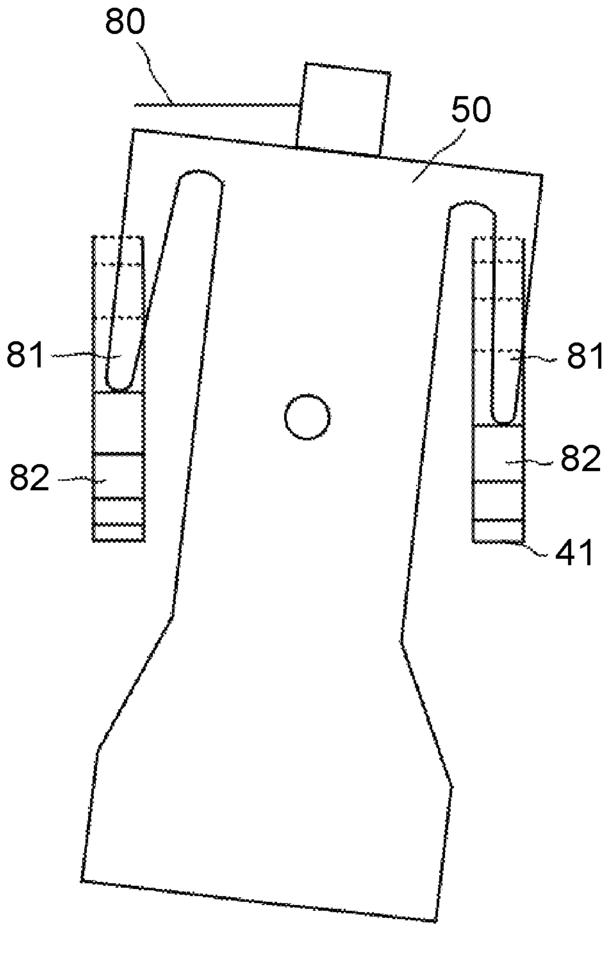
FIG. 6 is a partial schematic diagram of a driving mechanism according to an embodiment of the present invention.

In other embodiments of the present invention, as shown in FIG. 6, the driving unit 50 may further include two or more driving portions 81 while the driving wheel 40 includes two or more sub-wheels 82, and different driving portions 81 can be driven in cooperation with different sub-wheels 82. At this time, the linear actuator 80 can pull the driving unit 50 to push the wheel teeth 41 in the two directions of reciprocating rotation respectively, making the driving wheel 40 rotate. Therefore, there is no need to provide an elastic member.

In other embodiments of the present invention, the driving unit 50 may also be a gear cooperating with the driving wheel 40, which is not specifically limited herein.

Generally, after moving for a certain distance, the driving unit 50 needs to stop moving. Therefore, in order to determine the end point of the movement of the driving unit 50 in the driving direction, the driving unit 50 needs to trigger a first signal, indicating the end point of the driving direction, the first switch unit 21 receiving the first signal to turn off to cut off the power to the linear actuator 80. The program unit 10 provides with a timer electrically connected to the second switch unit 22, the timer controls the second switch unit 22 to turn off to cut off the power supply circuit. Preferably, in the embodiment of the present invention, the preset working time of the linear actuator 80 powered is T.

In other embodiments of the present invention, the driving mechanism further includes a blocking wall (like 171 in FIG. 2) which is used to determine the movement end of the driving unit 50 in the driving direction, that is, when the driving unit 50 contacts the blocking wall, the driving unit 50 reaches the movement end in the driving direction, which will be described below.

Preferably, in the embodiment of the present invention, after a blocking wall is provided in the driving mechanism, if time of the driving unit 50 rotating in the driving direction from the beginning to the contact with the blocking wall is t, then generally, $T \geq t$. That is, when the driving unit 50 contacts the blocking wall, the timer immediately stops timing, or continues to count the time $T-t$. Obviously, the shorter the $T-t$ time is, the shorter time the linear actuator 80 is powered, thus the lower the power consumption of the infusion device is. At the same time, this also reduces the time duration that the linear actuator 80 is powered, effectively reducing the possibility of fatigue fracture of the linear actuator 80, and improving the reliability of the infusion device. Preferably, $0\ \text{ms} \leq T-t \leq 30\ \text{ms}$. In one embodiment of the present invention, $T-t=5$ ms. In still another embodiment of the present invention, $T-t=10$ ms. In yet another embodiment of the present invention, $T-t=25$ ms.

It should be noted that in the embodiment of the present invention, the driving unit 50 includes multiple different movement modes, such as different movement speeds, different movement frequencies, or different movement amplitudes. For example, in an embodiment of the present invention, although the driving mechanism is provided with blocking wall, the infusion device can change the infusion mode according to the actual infusion demand, such as, the working time T of the timer is not long enough to make the driving unit 50 contact the blocking wall, that is, the movement and stopping of the driving unit 50 in the driving direction can also be controlled by the timer.

Figure 2:
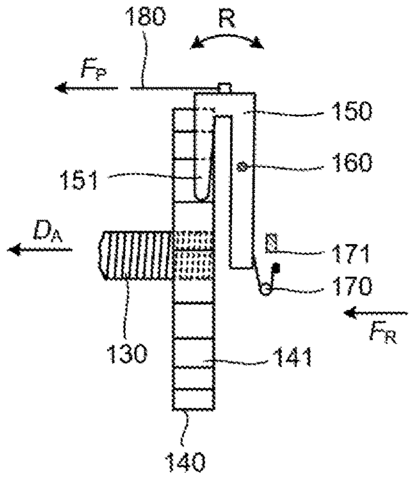
FIG. 2 is a partial schematic diagram of a driving mechanism providing with blocking wall according to an embodiment of the present invention.

FIG. 2 is a partial schematic diagram of a driving mechanism providing with blocking wall according to an embodiment of the present invention.

In the embodiment of the present invention, when the linear actuator 180 pulls the driving unit 150 by force $F_P$, the driving unit 150 rotates counter-clockwise around the rotating shaft 160 to push the wheel teeth 141 forward to drive the driving wheel 140 rotate, thereby driving the screw 130 to advance in the $D_A$ direction. At this time, the elastic member 170 generates an ever-increasing resetting and resilience force $F_R$. The driving mechanism is also provided with a blocking wall 171 for determining the movement end point of the driving unit 150 in the driving direction. After contacting the blocking wall 171, the driving unit 150 stops moving in the driving direction. When the timer stops working, the driving unit 150 resets and rotates clockwise around the shaft 160 under the action of the elastic force $F_R$.

Figure 3:
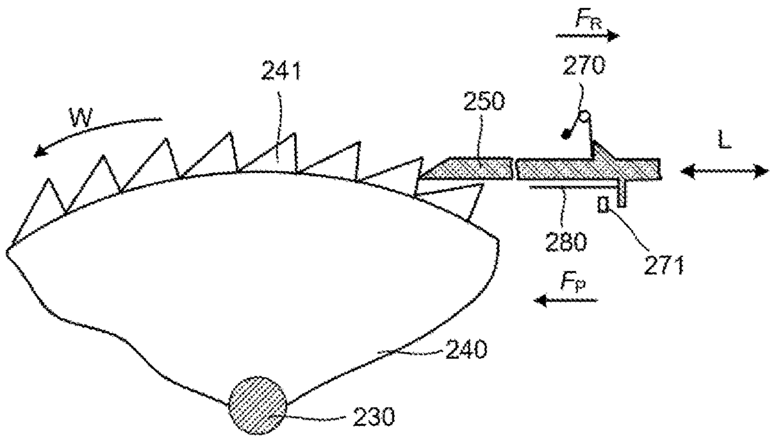
FIG. 3 is a partial schematic diagram of a driving mechanism providing with blocking wall according to another embodiment of the present invention.

FIG. 3 is a partial schematic diagram of a driving mechanism providing with blocking wall according to another embodiment of the present invention.

The linear actuator 280 and the elastic member 270 act on the driving unit 250 with the force $F_P$ and $F_R$, respectively, making the driving unit 250 linearly reciprocate in the L direction. Therefore, the driving unit 250 can push the wheel teeth 241 in the driving direction, making the driving wheel 240 move in W direction to realize drug infusion.

Similarly, a blocking wall 271 is provided in the driving mechanism. After moving in the linear driving direction and contacting the blocking wall 271, the driving unit 250 stops. When the timer stops working, the driving unit 250 resets under the force of the elastic member 270. The driving principle is similar to the foregoing said, which will not repeat herein.

Hereinafter, the circuit control principle of the driving mechanism will be described by taking the rotating reciprocating movement of the driving unit as an example.

Figure 4A:
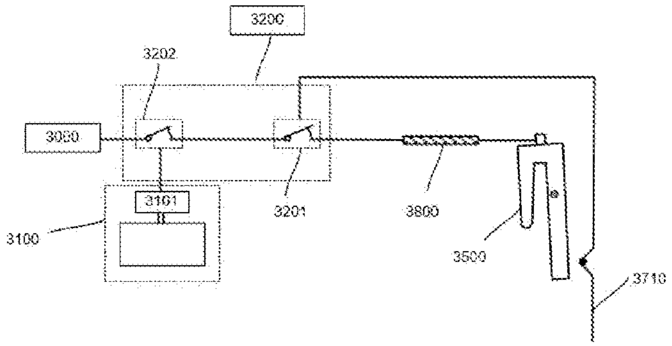
FIG. 4*a*-FIG. 4*d* are schematic diagrams of the control circuit of a driving mechanism according to an embodiment of the present invention.
Figure 4B:
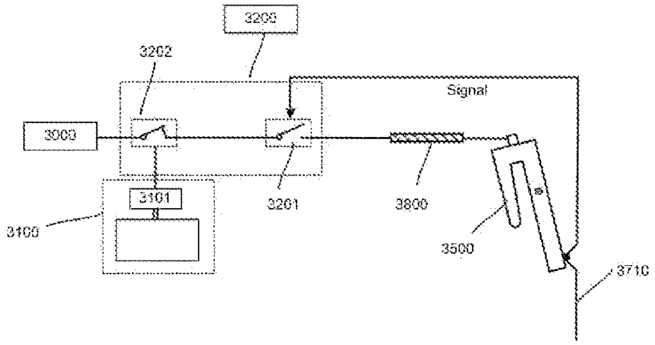
Figure 4C:
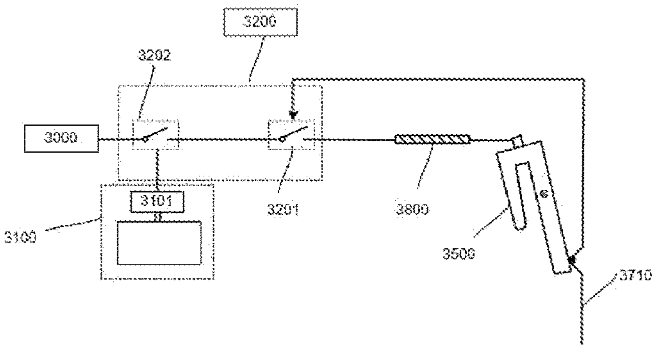

FIG. 4*a*-FIG. 4*c* are schematic diagrams of a driving mechanism control circuit according to an embodiment of the present invention.

Figure 4D:
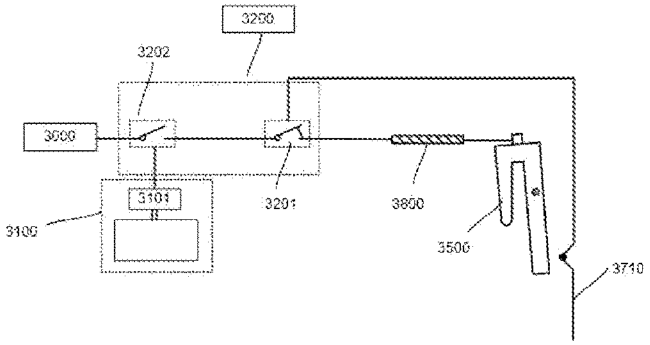

As shown in FIG. 4*a*, in the embodiment of the present invention, the power supply 3000, program unit 3100, the switch unit group 3200 and the linear actuator 3800 are electrically connected to form a power supply circuit for supplying power to the linear actuator 3800. The embodiment of the present invention is provided with a blocking wall 3710. At the initial state, the first switch unit 3201 and the second switch unit 3202 are closed, the linear actuator 3800 is powered, thus the driving unit 3500 is pulled to start moving in the driving direction until it contacts the blocking wall 3710, and the driving unit 3500 reaches the movement end in the driving direction. The time of the driving unit 3500 moving in the driving direction is t. After the driving unit 3500 contacts the blocking wall 3710, a first signal is triggered, the first switch unit 3201 receiving the signal to turn off to cut off the power to the linear actuator 3800, since the linear actuator 3800 does not immediately withdraw or remove the tension after the power is off (because of the material phase change taking a certain time), the linear actuator 3800 will not leave the blocking wall 3710 immediately, as shown in FIG. 4*b*. The timer 3101 continues to work until the preset working time reaches T, the timer 3101 controls the second switch unit 3202 to turn off to cut off the power supply circuit, during this process, no electrical signal is transmitted to the program unit 3100, as shown in FIG. 4*c*. Subsequently, under the elastic member (not shown in FIG. 4*a*-FIG. 4*c*), the driving unit 3500 withdraws the contact with blocking wall 3710, moving in the resetting direction, at that time, the first switch unit 3201 is closed while the second switch unit 3202 is in an open state until the next driving starts, as shown in FIG. 4*d*. Since the timer 3101 controls the second switch unit 3202 to turn off to cut off the power supply circuit, the linear actuator 3800 still cannot be powered, thus the driving unit 3500 resets. When the next power supply starts, the second switch unit 3202 turned on, making the linear actuator 3800 powered by the power supply 3000 again.

In the embodiment of the present invention, when the driving unit 3500 contacts the blocking wall 3710, a first signal is triggered, the first switch unit 3201 receiving the signal to turn off to cut off the power to the linear actuator 3800, compared to the driving mechanism control circuit without first switch unit 3201, until the timer 3101's working time reaches to the preset time T, the powered time to the linear actuator can be shortened by T−t, thus reduces the power consumption of the linear actuator 3800, also reduces the probability of fatigue fracture of the linear actuator 3800, improving the safety of the infusion reliability of the infusion device.

Figure 5A:
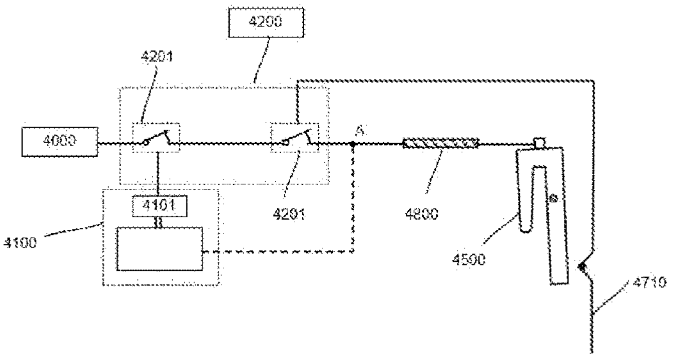
FIG. 5*a*-FIG. 5*d* are schematic diagrams of the control circuit of a driving mechanism according to another embodiment of the present invention.
Figure 5B:
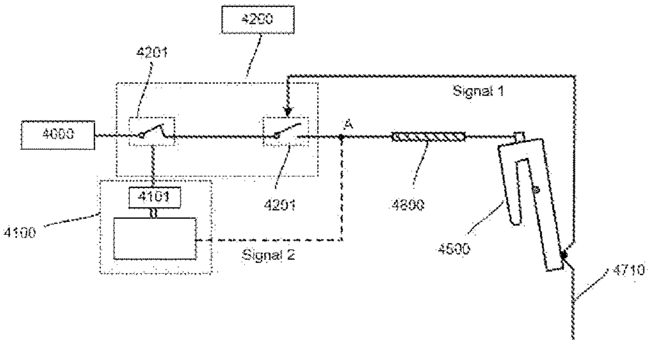
Figure 5C:
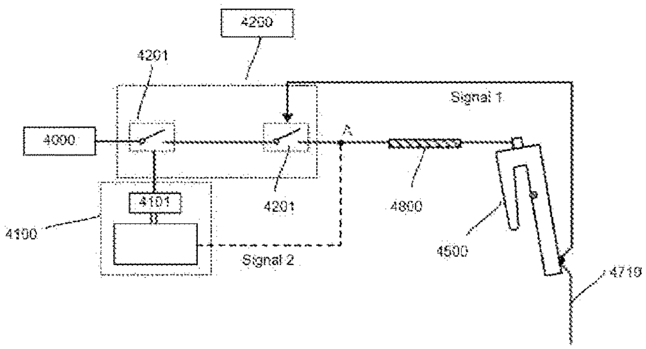

FIG. 5*a*-FIG. 5*c* are schematic diagrams of a driving mechanism control circuit according to an embodiment of the present invention.

As shown in FIG. 5*a*, in the embodiment of the present invention, the power supply 4000, program unit 4100, the switch unit group 4200 and the linear actuator 4800 are electrically connected to form a power supply circuit for supplying power to the linear actuator 4800. The embodiment of the present invention is provided with a blocking wall 3710. The movement mode of the driving unit 4500 is similar to the foregoing said. At the initial state, the first switch unit 4201 and the second switch unit 4202 are closed, the linear actuator 4800 is powered, the electrical connection point A is located on the power supply circuit between the first switch unit 4201 and the linear actuator 4800. The program unit 4100 is electrically connected to the electrical connection point A to obtain the second signal. Preferably, the second signal is also a voltage signal. Before the driving unit 4500 contacts the electrical blocking wall 4710, the electrical connection point A is at a low voltage state.

As shown in FIG. 5*b*, when the driving unit 4500 contacts the blocking wall 4710, and the driving unit 4500 reaches the movement end in the driving direction. The time of the driving unit 4500 moving in the driving direction is t. After the driving unit 4500 contacts the blocking wall 4710, a first signal is triggered, the first switch unit 4201 receiving the signal to turn off to cut off the power to the linear actuator 4800, since the linear actuator 4800 does not immediately withdraw or remove the tension after the power is off (because of the material phase change taking a certain time), the linear actuator 4800 will not leave the blocking wall 4710 immediately, the voltage of the electrical connection point A will be the same as the electrical contact point of driving unit 4500 and the blocking wall 4710, that is, maintains a high voltage state. Therefore, before and after the first switch unit 4200 is turned off, the voltage of the electrical connection point A is different, thus a second signal is generated and sent to the program unit 4100. Obviously, in the embodiment of the present invention, the second signal is a voltage changing signal. The timer 4101 continues to work until the preset working time reaches T, the timer 4101 controls the second switch unit 4202 to turn off to cut off the power supply circuit as shown in FIG. 5*c*.

Figure 5D:
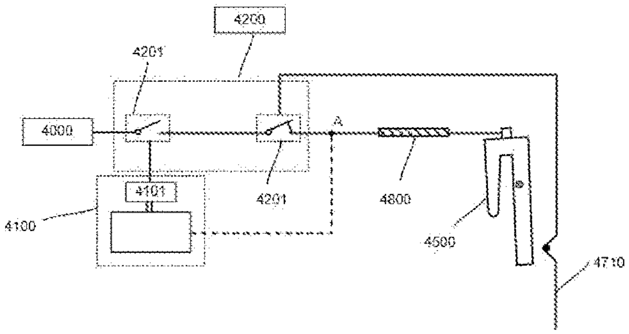

As shown in FIG. 5*d*, after the linear actuator 4800 releases the tension, the driving unit 4500 leaves the blocking wall 4710 under the force of the elastic member, the electrical contact of the driving unit 4500 land the blocking wall 4710 returns to the initial high voltage state, and the first switch unit 4201 is turned on again, and the second switch is opened until the next driving starts, as shown in FIG. 5*d*. Since the timer 4101 controls the second switch unit 4202 to turn off to cut off the power supply circuit, the linear actuator 4800 still cannot be powered, thus the driving unit 4500 resets. When the next power supply starts, the second switch unit 4202 turns on, making the linear actuator 4800 powered by the power supply 4000 again.

In the embodiment of the present invention, the program unit 4100 can continuously adjusts the preset time of the timer 4101 through the received electrical signal from the electrical connection point A, making the preset time T of the timer infinitely close to t, which reduces the power consumption of the infusion device and improves the reliability of the infusion device.

In summary, the present invention discloses a driving mechanism of a drug infusion device. The first switch unit controls the power to the linear actuator directly, and the timer controls the power supply circuit by the second switch unit, reducing the power consumption of the infusion device.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. A drive mechanism of a drug infusion device, comprising:
- at least one driving unit and at least one driving wheel, wherein the driving unit, moving in a driving direction, drives the driving wheel to rotate;
- a linear actuator, electrically connected with the driving unit, pulling the driving unit to move in the driving direction after being powered;
- a switch unit group, comprising a first switch unit and a second switch unit, the first switch electrically connected with the linear actuator;
- a power supply, wherein the power supply, the switch unit group and the linear actuator are electrically connected to form a power supply circuit that supplies power to the linear actuator, when the linear actuator is powered, the driving unit implements driving, and the driving unit triggers a first signal, indicating an end point of the driving direction, the first switch unit receiving the first signal to turn off the power to the linear actuator; and
- a program unit, including a timer electrically connected to the second switch unit, the timer controlling the second switch unit to turn off the power supply circuit.

2. A drive mechanism of a drug infusion device of claim 1, wherein
- the driving unit includes at least one driving portion, the driving wheel is provided with wheel teeth which are pushed by the driving portion to drive the driving wheel.

3. A drive mechanism of a drug infusion device of claim 2, wherein
- a movement mode of the driving unit includes a linear reciprocating movement or a rotary reciprocating movement.

4. A drive mechanism of a drug infusion device of claim 3, wherein
- the at least one driving portion includes two driving portions while the driving wheel includes two sub-wheels, and the two driving portions respectively cooperate with the two sub-wheels, and the driving unit drives the two sub-wheels to rotate in two directions of a reciprocating rotation.

5. A drive mechanism of a drug infusion device of claim 4, characterized in that,
- further comprising at least one blocking wall, and the driving unit reaches a movement end of the driving direction when contacting the blocking wall, and during a process of the driving unit moving in the driving direction, a movement time of the driving unit is t while a working time of the timer is T, then T≥t.

6. A drive mechanism of a drug infusion device of claim 5, wherein $$0\text{ ms} \leq T-t \leq 30\text{ ms}.$$

7. A drive mechanism of a drug infusion device of claim 4,
- further comprising an elastic member, and a reciprocating movement includes the driving direction and a resetting direction, and the elastic member applies a resetting and resilience force to the driving unit.

8. A drive mechanism of a drug infusion device of claim 4,
- further comprising an electrical connection point located on the power supply circuit between the linear actuator and the first switch unit, wherein the program unit is electrically connected to the electrical connection point to obtain a second signal, a voltage changing signal, of the electrical connection point.

9. A drive mechanism of a drug infusion device of claim 1, wherein
- the switch unit includes a MOS field effect transistor, an analog switch or a relay.

10. A drive mechanism of a drug infusion device of claim 1, wherein
- the linear actuator is a shape memory alloy.

11. A drive mechanism of a drug infusion device of claim 3, wherein
- the driving unit includes a variety of different reciprocating frequencies, a variety of different reciprocating speeds, or a variety of different movement amplitudes.

* * * * *